US010327735B2

(12) United States Patent
Cho et al.

(10) Patent No.: US 10,327,735 B2
(45) Date of Patent: Jun. 25, 2019

(54) PORTABLE ULTRASONIC PROBE HAVING A FOLDER PART

(71) Applicant: SAMSUNG ELECTRONICS CO., LTD., Suwon-si (KR)

(72) Inventors: Kyung Il Cho, Seoul (KR); Jong Keun Song, Yongin-si (KR); Bae Hyung Kim, Yongin-si (KR); Young Il Kim, Suwon-si (KR); Seung Heun Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1415 days.

(21) Appl. No.: 14/301,540

(22) Filed: Jun. 11, 2014

(65) Prior Publication Data

US 2014/0364741 A1 Dec. 11, 2014

(30) Foreign Application Priority Data

Jun. 11, 2013 (KR) ........................ 10-2013-0066434

(51) Int. Cl.
*A61B 8/00* (2006.01)

(52) U.S. Cl.
CPC .................................. *A61B 8/4427* (2013.01)

(58) Field of Classification Search
None
See application file for complete search history.

(56) References Cited

U.S. PATENT DOCUMENTS

| | | | | |
|---|---|---|---|---|
| 5,721,463 A * | 2/1998 | Snyder | A61B 8/546 | 310/327 |
| 5,924,988 A * | 7/1999 | Burris | A61B 8/00 | 600/437 |
| 6,122,538 A * | 9/2000 | Sliwa, Jr. | A61B 8/00 | 600/459 |
| 6,540,685 B1 * | 4/2003 | Rhoads | A61B 8/00 | 600/459 |
| 2002/0035328 A1 * | 3/2002 | Roundhill | A61B 8/14 | 600/443 |
| 2003/0013966 A1 | 1/2003 | Barnes et al. | | |
| 2003/0078501 A1 * | 4/2003 | Barnes | A61B 5/0402 | 600/446 |
| 2003/0195418 A1 | 10/2003 | Barnes et al. | | |
| 2004/0015079 A1 * | 1/2004 | Berger | A61B 8/546 | 600/437 |
| 2008/0218743 A1 * | 9/2008 | Stetten | A61B 8/0833 | 356/73 |
| 2010/0274131 A1 | 10/2010 | Barnes et al. | | |

(Continued)

FOREIGN PATENT DOCUMENTS

| | | | |
|---|---|---|---|
| KR | 10-2010-0057341 A | 5/2010 | |
| KR | 10-0969545 B1 | 7/2010 | |

(Continued)

*Primary Examiner* — Joel F Brutus
(74) *Attorney, Agent, or Firm* — Sughrue Mion, PLLC

(57) ABSTRACT

Provided is a portable ultrasonic probe including a main body comprising a transducer configured to generate an ultrasonic wave, and a folder part comprising a display and rotatably coupled to an end portion of the main body, wherein the main body further comprises an analog to digital (AD) converter and a beamformer, the AD converter and the beamformer being provided in a chip.

20 Claims, 17 Drawing Sheets

(56) References Cited

U.S. PATENT DOCUMENTS

2012/0060610 A1* 3/2012 Oaks .................... A61B 8/4444
73/632
2012/0065508 A1* 3/2012 Gerard ..................... A61B 8/08
600/443
2012/0065510 A1* 3/2012 Snare ........................ A61B 8/14
600/443
2012/0179043 A1* 7/2012 Kim .................... G01S 7/52017
600/447
2015/0038841 A1* 2/2015 Ichimura .............. A61B 8/4427
600/437

FOREIGN PATENT DOCUMENTS

KR 10-0992446 B1 11/2010
KR 10-1116950 B1 3/2012

* cited by examiner

PORTABLE ULTRASONIC PROBE HAVING A FOLDER PART

CROSS-REFERENCE TO RELATED APPLICATION

This application claims priority from Korean Patent Application No. 2013-0066434, filed on Jun. 11, 2013, in the Korean Intellectual Property Office, the disclosure of which is incorporated herein by reference in its entirety.

BACKGROUND

1. Field

Apparatuses and methods consistent with exemplary embodiments relate to an ultrasonic probe of a ultrasonic diagnostic apparatus configured to diagnose a disease.

2. Description of the Related Art

An ultrasonic diagnostic apparatus refers to an apparatus that obtains a cross section of a soft tissue or an image of a blood flow in a non-invasive manner by radiating ultrasonic waves toward a target portion inside a subject from a surface of the subject and receiving a reflected ultrasonic echo signal.

The ultrasonic diagnostic apparatus, when compared other image diagnostic apparatuses such as, for example, an X-ray apparatus, a computerized tomography scanner (CT scanner), a magnetic resonance image (MRI), and a nuclear medicine diagnostic apparatus, is provided in a small size, less expensive, and is capable of displaying a diagnostic image in real time. In addition, since the ultrasonic diagnostic apparatus does not cause radiation exposure, a higher level of safety may be provided. Thus, in addition to the field of gynecology, the ultrasonic diagnostic apparatus is widely used in various fields such as, for example cardiac diagnosis, abdominal diagnosis, and urological diagnosis.

The ultrasonic diagnostic apparatus includes an ultrasonic probe configured to radiate an ultrasonic wave toward a subject to obtain an image of an inside of the subject, and receive an ultrasonic echo signal that is reflected from the subject.

SUMMARY

One or more exemplary embodiments provide a portable ultrasonic probe which enables a user to check an image more easily.

One or more exemplary embodiments also provide an ultrasonic probe provided with a structure to release heat generated therefrom.

In accordance with an aspect of an exemplary embodiment, a portable ultrasonic probe includes a main body and a folder part. The main body may include a transducer configured to generate an ultrasonic wave. The folder part may include a display and may be rotatably coupled to an end portion of the main body. The main body may include an analog to digital (AD) converter and a beamformer that are provided in a chip.

In accordance with an aspect of another exemplary embodiment, an ultrasonic system includes a portable ultrasonic probe and a backend part. The portable ultrasonic probe may include a first communicator configured to transmit data output from a beamformer. The backend part may include a second communicator to receive the data transmitted from the first communicator, and a display to display an ultrasonic image based on the data received by the second communicator.

In accordance with an aspect of still another exemplary embodiment, a portable ultrasonic probe includes a main body including at least one ultrasonic element configured to generate an ultrasonic wave; and a foldable part rotatably coupled to the main body, wherein the main body further includes an analog to digital (AD) converter, and wherein a digital beamformer is provided in one of the main body and the foldable.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Figure 1:
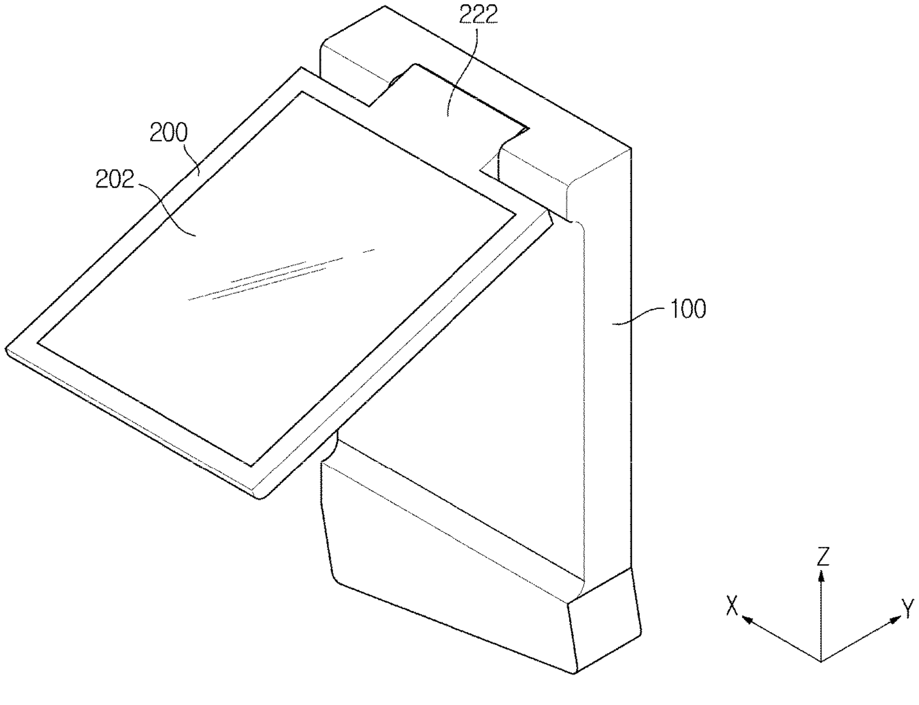
FIG. 1 is a perspective view showing an exterior appearance of a portable ultrasonic probe according to an exemplary embodiment.

Hereinafter, exemplary embodiments will now be described more fully with reference to the accompanying drawings. The exemplary embodiments may, however, be embodied in many different forms and should not be construed as being limited to the embodiments set forth herein; rather, these embodiments are provided so that this disclosure will be thorough and complete, and will fully convey the scope of the disclosure to those skilled in the art. For example, configuring elements that are singular forms may be executed in a distributed fashion, and also, configuring elements that are distributed may be combined and then executed. In the following description, well-known functions or constructions are not described in detail since they would obscure the disclosure with unnecessary detail. Also, throughout the specification, like reference numerals in the drawings denote like elements.

Figure 2:
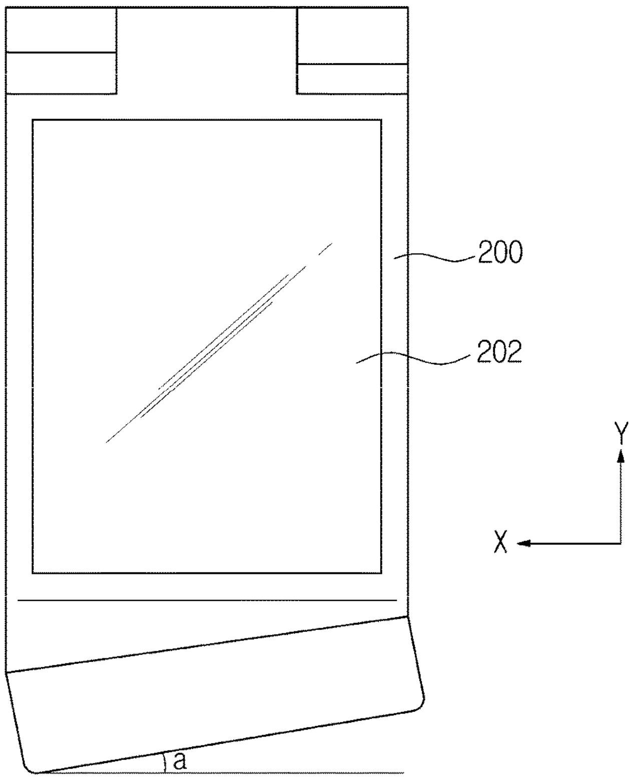
FIG. 2 is a front view showing a portable ultrasonic probe according to an exemplary embodiment.

FIG. 1 is a perspective view showing an exterior appearance of a portable ultrasonic probe according to an exemplary embodiment, FIG. 2 is a front view showing a portable ultrasonic probe according to an exemplary embodiment, and FIGS. 3 to 7 are blocked diagrams showing a configuration of a portable ultrasonic probe according to various exemplary embodiments.

Referring to FIG. 1, a portable ultrasonic probe includes a main body 100 having a transducer 101 (see FIG. 3) to generate an ultrasonic wave, and a folder part 200 rotatably coupled to the main body 100 and having a display 202 to display an ultrasonic image.

Figure 3:
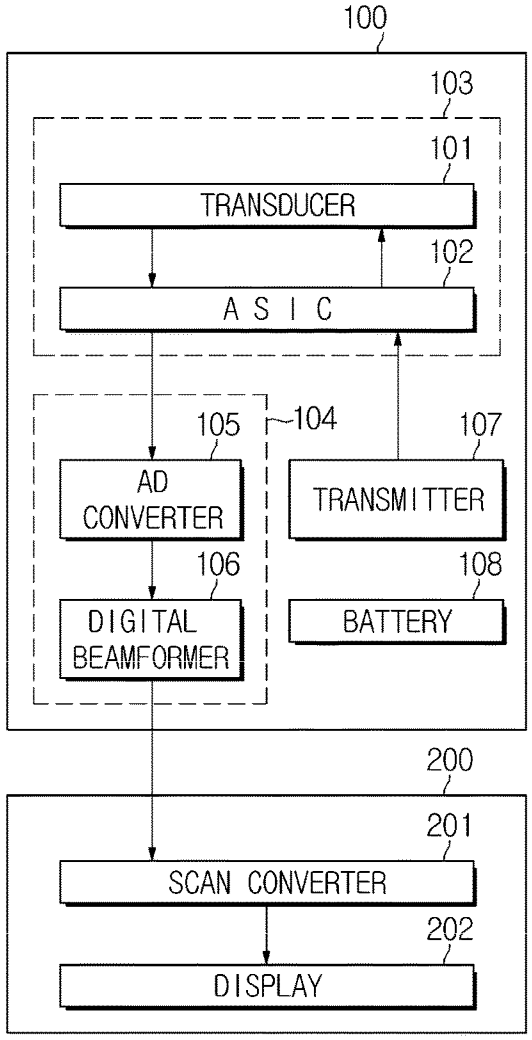
FIGS. 3 to 7 are blocked diagrams showing a configuration of a portable ultrasonic probe according to various exemplary embodiments.

Referring to FIG. 3, the main body 100 includes a transducer module 103 to generate an ultrasonic wave, a beamformer 104 to perform beamforming on an ultrasonic echo signal received from the transducer module 103, a transmitter 107 to output an electrical signal to the transducer module 103 such that ultrasonic wave may be generated and radiated by the transducer module 103, and a battery 108 to supply power to drive the portable ultrasonic probe.

The transducer module 103 includes the transducer 101 configured to generate an ultrasonic wave. As one example of the transducer 101, a magnetostrictive ultrasonic transducer using an magnetostrictive effect of a magnetic substance, or a piezoelectric ultrasonic transducer using a piezoelectric effect of a piezoelectric substance may be used. Additionally, a capacitive micromachined ultrasonic transducer (hereinafter, referred to as "cMUT"), configured to receive and/or transmit an ultrasonic wave by using vibrations of hundreds or thousands of micromachined thin films may be used as the transducer 101. Herein, for illustrative purposes, the cMUT will be described as an example of the transducer 101.

In addition, the transducer module 103 includes an application specific integrated circuits (ASIC) 102 in which an array of the cMUTs is bonded using a flip-chip bonding method. The ASIC 102 in which the cMUT array is bonded may be provided with a signal line bonded to a board 115 (see FIG. 10) in a wire bonding method, or electrically connected to the board 115 via a flexible printed circuit board. The board 115 may include the transmitter 107, and may adjust the generation of an ultrasonic wave because an electrical signal applied to the cMUT array may be controlled according to the logic of the ASIC 102 when an electrical signal is applied through the transmitter 107 of the board 115.

The beamformer 104 configured to perform beamforming on the ultrasonic echo signal output from the transducer module 103 includes an analog to digital (AD) converter 105 to convert the ultrasonic echo signal into a digital signal, and a digital beamformer 106 to perform beamforming on the ultrasonic echo signal, which is converted into a digital signal and output from the AD converter 105. When the echo ultrasonic wave is returned after being reflected from the same target portion, the time at which the echo ultrasonic wave is received may be varied. That is, with respect to the echo ultrasonic waves received from the same target portion, a predetermined time difference may be present between the echo ultrasonic waves because a distance between the target portion and elements of the transducer 101 configured to receive echo the ultrasonic waves may not be the same. Thus, echo ultrasonic waves that are received by the elements of the transducer 101 at each different time may be echo ultrasonic waves that are generated by ultrasonic waves radiated by the transducer module 103 toward the same target portion at the same time. Accordingly, the digital beamformer 106 may calibrate time difference between ultrasonic echo signals. For example, by delaying an echo ultrasonic wave that is input through a certain channel, the time difference may be calibrated, and the ultrasonic echo signals with calibrated time difference may be collected.

In the above, it is described that the ultrasonic echo signals that are output from the transducer module 103 are converted into digital signals, and beamforming is performed on the digital signals by the digital beamformer 106, however, exemplary embodiments are not limited hereto. For example, the portable ultrasonic probe may include an analog beamformer to perform an analog beamforming. That is, ultrasonic echo signals output from the transducer module 103 may be received by the analog beamformer such that the time difference is calibrated, and the ultrasonic echo signals with calibrated time difference may be converted into digital signals by the AD converter 105. Next, the above described beamforming process may be performed on the digital signals by the digital beamformer 106.

The beamformer 104 having the above described beamformer or the digital beamformer 106, and the AD converter 105 may be implemented into a single chip and provided at the main body 100 of the portable ultrasonic probe according to an exemplary embodiment.

The transducer module 103 and the beamformer 104 may be provided in a single module and detachably provided at the main body 100.

At the main body 100, the battery 108 configured to supply power to drive the portable ultrasonic probe may be provided. The battery 108 may be detachably provided at the main body 100 such as a battery that is mounted on a cellular phone. The battery 108 may be included in the folder part 200. When the battery 108 is included in the folder part 200, the weight of the folder part 200 may be increased, and the increased weight may act as a load to a rotational movement of the folder part 200. Therefore, the battery 108 may be included in the main body 100.

The folder part 200 includes a scan converter 201 and the display 202.

The scan converter 201 is configured to receive digital data that is output from the beamformer 104 of the main body 100 and output the digital data to the display 202 such that an ultrasonic image is displayed. In general, the direction of a scan of an image and the direction of a scan of the display 202 are substantially perpendicular to each other, and thus there is a need to change a scan direction to display an image on the display 202. An operation of changing the scan direction may be performed by the scan converter 201.

The display 202 is provided at a surface opposite to a surface of the folder part 200 that comes into contact with the main body 100 when the folder part 200 is in a closed position. Thus, as illustrated in FIG. 1, a user may check an ultrasonic image displayed on the display 202 by examining a subject when the portable ultrasonic probe is open by rotating the folder part.

Referring to FIG. 2, a surface from which an ultrasonic wave of the transducer 101 included at the main body 100 is radiated is provided to form a predetermined angle 'a' with respect to an x-axis. That is, a ultrasonic wave irradiation surface is a top surface of the portable ultrasonic probe are not parallel to each other, but the ultrasonic irradiation surface is formed in an inclined manner with respect to the top surface of the portable ultrasonic probe.

As illustrated in FIG. 2, when the ultrasonic irradiation surface is provided as the above, a user may easily check the display 202 of the folder part 200 when examining a subject with the folder part 200 being opened. That is, when the inclined ultrasonic irradiation surface comes into contact with an examination portion of a subject, the display 202 of the folder part 200 is inclined toward a user according to a degree by which the ultrasonic irradiation surface is inclined. Thus, the user may easily check the image displayed on the display 202 without having to change the user's posture to check the display 202 or tilt the ultrasonic probe while proceeding with the examination.

Figure 4:
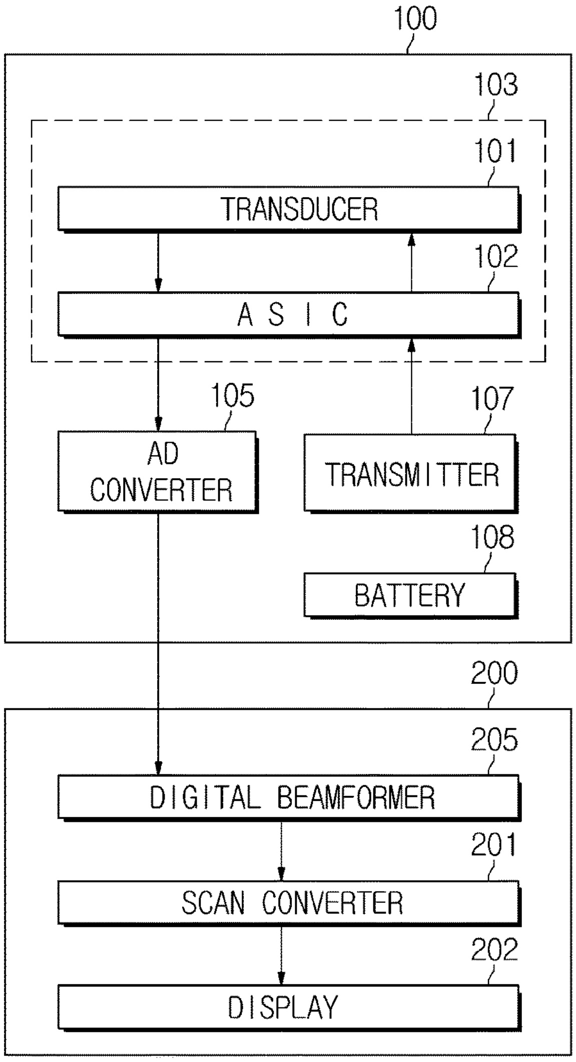

Referring to FIG. 4, according to another exemplary embodiment, the main body 100 of the portable ultrasonic probe includes the transducer module 103 configured to generate an ultrasonic wave, the AD converter 105 configured to convert the ultrasonic echo signal received from the transducer module 103 into a digital data, the transmitter 107 configured to output an electrical signal such that an ultrasonic wave may be generated and radiated from the transducer module 103, and the battery 108 configured to supply power to drive the portable ultrasonic probe.

Compared with the embodiment illustrated in FIG. 3, in the exemplary embodiment of FIG. 4, the beamformer is not provided at the main body 100, but is provided at the folder part 200.

That is, when the ultrasonic echo signal output from the transducer module 103 is converted into digital signal by the AD converter 105, the converted signal is subject to beamforming by a digital beamformer 205 provided at the folder part 200.

The scan converter 201 of the folder part 200 receives the digital data output from the digital beamformer 205, and outputs the received digital data such that an ultrasonic image is displayed on the display 202.

In FIG. 4, ultrasonic eco signals that are output from the transducer module 103 are first converted into digital signals, but exemplary embodiments are not limited hereto. For example, the main body 100 may include an analog beamformer such that an analog beamforming is performed on the ultrasonic eco signals. That is, the ultrasonic echo signal output from the transducer module 103 may be received by the analog beamformer to calibrate the time difference, and the ultrasonic echo signal with calibrated time difference may be converted into a digital signal by the AD converter 105, and then the converted digital signal is subject to digital beamforming by the digital beamformer 205 provided at the folder part 200.

The descriptions with respect to elements or configurations that are the same or similar to those already described with reference to FIG. 3 will be omitted.

Figure 5:
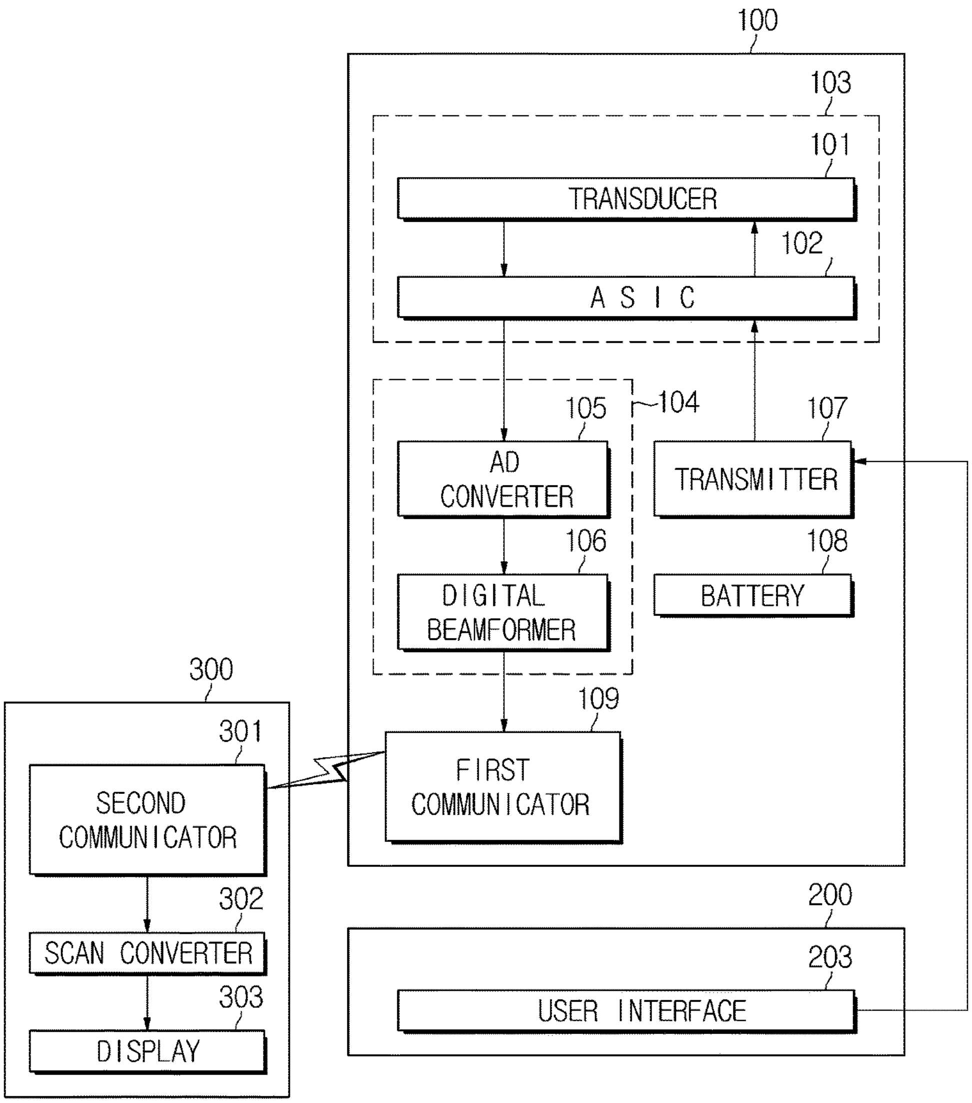

Referring to FIG. 5, the main body 100 of the portable ultrasonic probe includes the transducer module 103 configured to generate an ultrasonic wave, the beamformer 104 configured to perform beamforming on the ultrasonic echo signal received from the transducer module 103, the transmitter 107 to output an electrical signal such that an ultrasonic echo signal may be generated and radiated from the transducer module 103, the battery 108 configured to supply power to drive the portable ultrasonic probe, and a first communicator 109 to transmit data that is output from the beamformer 104 to a backend part 300.

In FIG. 5, an ultrasonic image is not displayed on the folder part 200 of the portable ultrasonic probe, but is displayed on a display 303 of the backend part 300 separately provided from the portable ultrasonic probe. That is, the data output from the beamformer 104 is not transmitted to the folder part 200, but is transmitted to the backend part 300 through the first communicator 109 and is displayed as an ultrasonic image on the display 303 provided at the backend part 300. Thus, the main body 100 of the portable ultrasonic probe includes the first communicator 109 capable of performing a communication with a second communicator 301 of the backend part 300. A method of communication between the first communicator 109 and the second communicator 301 may include a cable method or a wireless method may be used. When the portability of the portable ultrasonic probe is considered, the communication may be preferably performed by use of the wireless communication method.

The folder part 200 includes the display 202 implemented by use of, for example, a touch panel, and the display 202 may provide a user interface configured to manipulate the portable ultrasonic probe. Information that is input through the user interface with respect to the radiation of an ultrasonic wave is output to the transmitter 107 of the main body 100, and the transmitter 107 generates a control signal to radiate the ultrasonic wave according to the information and outputs the control signal to the transducer module 103.

In this embodiment, an ultrasonic image is displayed at a separate apparatus that is separated from the portable ultrasonic probe, that is, the backend part 300, but exemplary embodiments do not exclude a case displaying an ultrasonic image on the display 202 of the folder part 200. That is, a user may select an ultrasonic image to be displayed on a desired structure, that is, the backend part 300 or the folder part 200.

The backend part 300 includes the second communicator 301 configured to receive data transmitted from the first communicator 109, a scan converter 302 configured to change the scan direction of the data, which is received from the first communicator 109, and to output the data to the display 303, and the display 303 configured to display an ultrasonic image when the data is output from the scan converter 302.

The backend part 300 may be a work station that is used at a general ultrasonic diagnostic apparatus provided with the display 303 connected to the portable ultrasonic probe via wireless or a cable to display an ultrasonic image. However, any apparatus provided with the display 303 capable of displaying an ultrasonic image may be included in the backend part 300 of this embodiment.

In FIG. 5, the first communicator 109 is illustrated to be included in the main body 100, but this is only one example, and the first communicator 109 may be provided at the folder part 200 or may be provided at the folder part 200 together with the digital beamformer 106.

Figure 6:
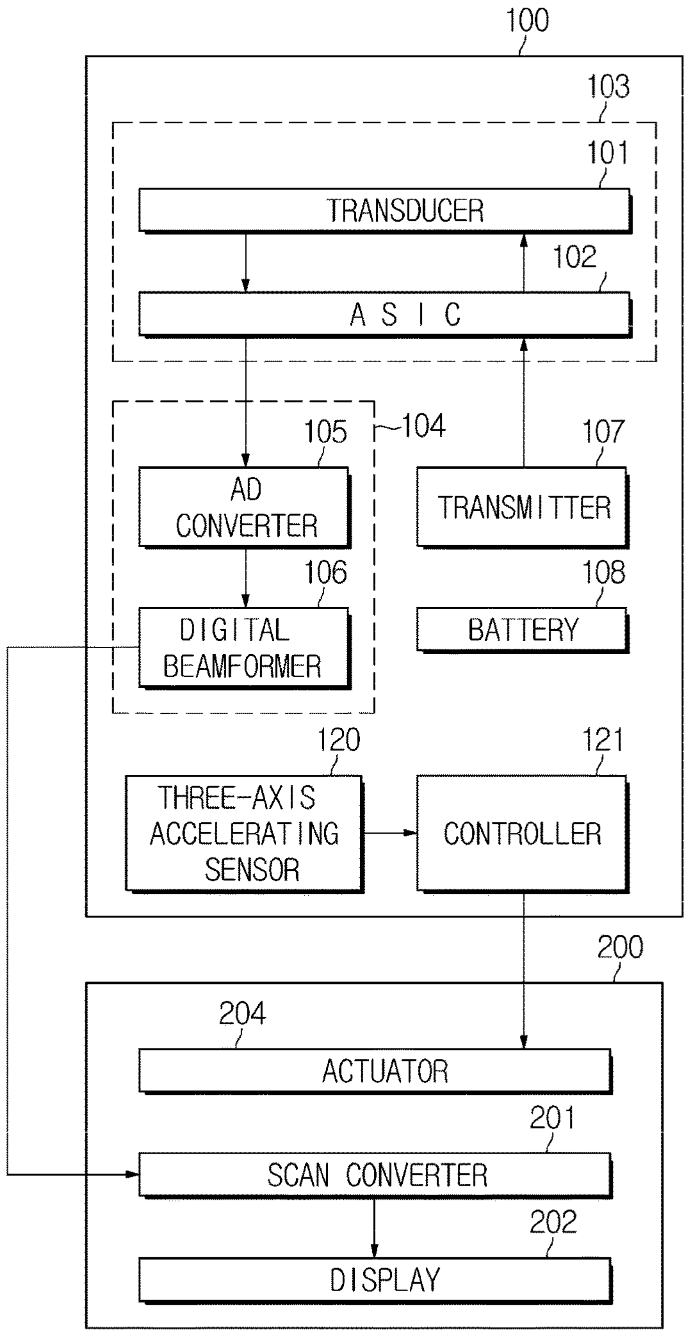

Referring to FIG. 6, the main body 100 includes the transducer module 103 configured to generate an ultrasonic wave, the beamformer 104 configured to perform beamforming on the ultrasonic echo signal that is received from the transducer module 103, the transmitter 107 configured to output an electrical signal such that an ultrasonic wave may be generated and radiated from the transducer module 103, the battery 108 configured to supply power to drive the portable ultrasonic probe, a three-axis accelerating sensor 120 configured to detect the degree of an inclination of the main body 100, that is, the inclination of the main body 100, and a controller 121 configured to output a driving signal to rotate the folder part 200 based on inclination information of the main body 100, that is, inclination information that is detected by the three-axis accelerating sensor 120. Here, the controller 121 may include a central processing unit (CPU).

The folder part 200 includes an actuator 204 configured to rotate the folder part 200 according to the driving signal output from the controller 121 of the main body 100, the scan converter 201 configured to change the scan direction of the data, which is received from the beamformer 104, and to output the data to the display 202, and the display 202 configured to display an ultrasonic image when the data is output from the scan converter 201.

The three-axis accelerating sensor 120 mounted on the main body 100 is configured to detect the degree of inclination of the main body 100 when the portable ultrasonic probe is operated. When the degree of inclination of the main body 100 is detected by the three-axis accelerating sensor 120, the controller 121, to rotate the folder part 200 such that the display 202 of the folder part 200 is headed toward a user, drives the actuator 204 provided at a coupler of the folder part 200 based on detected information, i.e., information about the degree of inclination of the main body. The actuator 204 rotates the folder part 200 according to the control of the controller 121, such that the display 202 may face a user.

When the ultrasonic probe is moved along the surface of a subject, which may be in a curved shape, during an ultrasonic examination, the degree of inclination of the main body 100 is changed according to the degree of curvature of the subject.

When the main body 100 is inclined toward a side opposite to a user, the folder part 200 is also inclined accordingly, and thus the user needs to rotate the folder part 200 toward a direction opposite to the direction of inclination of the folder part 200, such that the user may check an ultrasonic image.

To perform a manipulation as the above each time the degree of inclination of the main body 100 is changed may be inconvenient, and thus this embodiment uses the three-axis accelerating sensor 120 to detect the degree of inclination of the main body 100. Based on the detected degree of inclination, the display 202 of the folder part 200 is controlled to automatically adjust the direction thereof to face toward a user. A user, prior to starting an ultrasonic examination, may open the folder part 200, and rotate the folder part 200 to a position at which the user may easily check the display 202. When the ultrasonic examination is started, the controller 121 sets an initial position of the folder part 200 when the ultrasonic examination is started as a target position, and when the position of the folder part 200 differs from the target position because the degree of inclination of the main body 100 is changed, the controller 121 may output a control signal to rotate the folder part 200 to return to the target position the actuator 204 based on the information detected by the three-axis accelerating sensor 120. Thus, the folder part 200 may be rotated to be at the target position.

Figure 17:
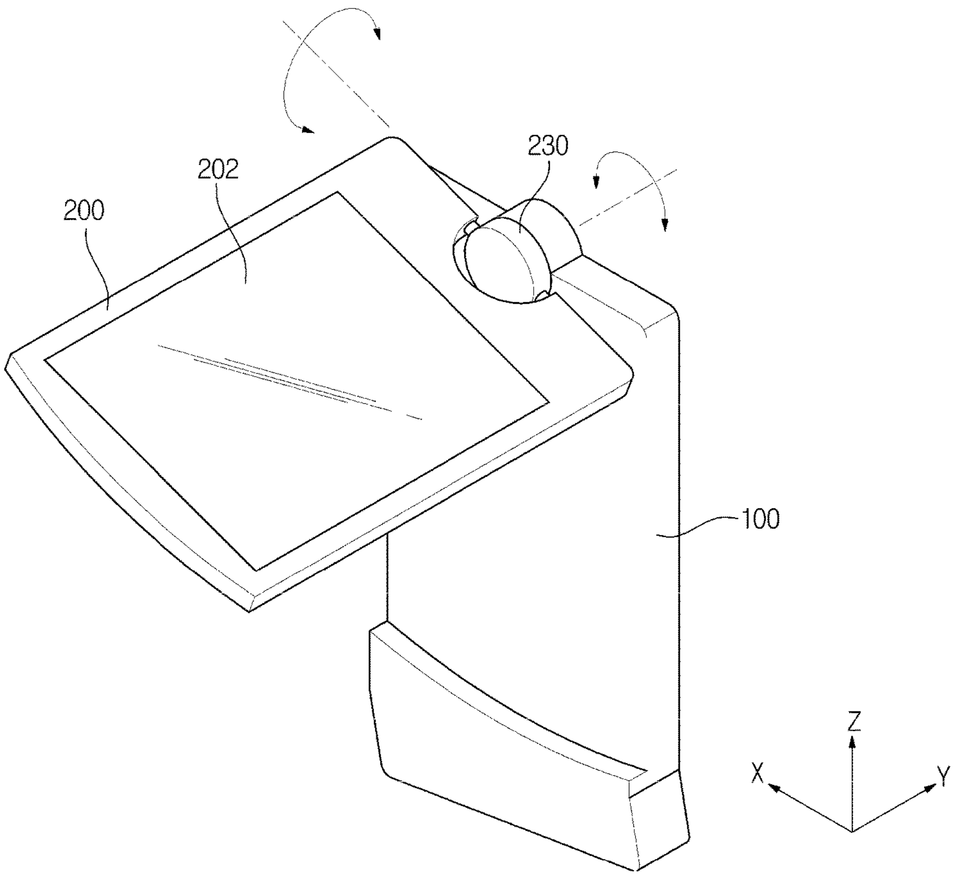
FIG. 17 is a perspective view showing an exterior appearance of a portable ultrasonic probe according to still another exemplary embodiment.

FIG. 17 is a perspective view showing an exterior appearance of a portable ultrasonic probe according to still another exemplary embodiment. As illustrated in FIG. 17, a coupler 230 of the folder part 200 of an exemplary embodiment may be provided with two rotating axes that are substantially perpendicular to each other, e.g., a first rotating axis parallel to a y-axis and a second rotating axis that is substantially perpendicular to the first rotating axis.

When the coupler 230 is provided with the first rotating axis and the second rotating axis, the folder part 200 may be rotated as illustrated in FIG. 17. By rotating the folder part 200 around the first rotating axis and the second rotating axis, the folder part 200 may be adjusted to have a target position.

Figure 7:
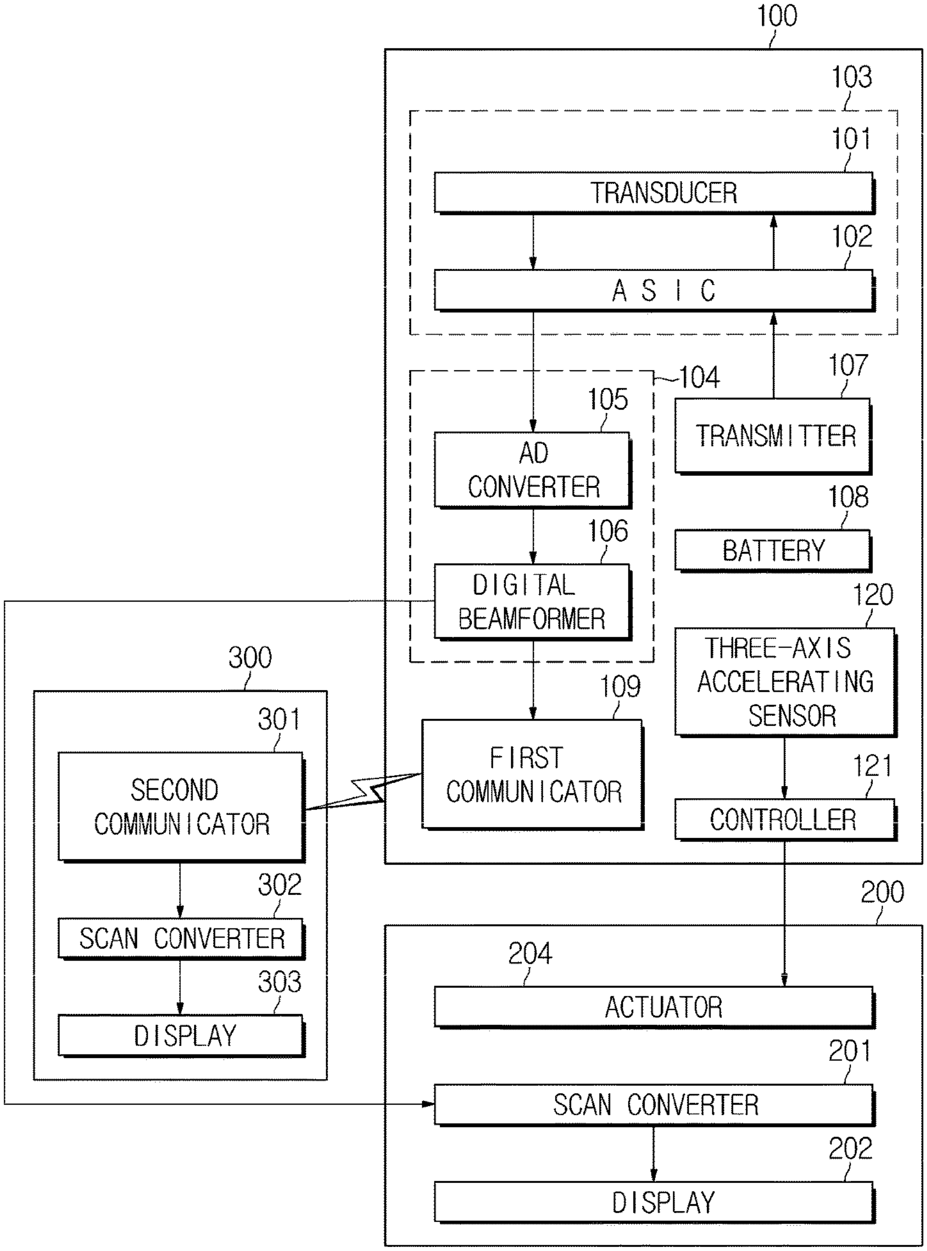

Referring to FIG. 7, the main body 100 includes the transducer module 103 configured to generate an ultrasonic wave, the beamformer 104 configured to perform beamforming on the ultrasonic echo signal that is received from the transducer module 103, the transmitter 107 configured to output an electrical signal such that an ultrasonic wave may be generated and radiated from the transducer module 103, the battery 108 configured to supply power to drive the portable ultrasonic probe, the first communicator 109 to transmit data that is output from the beamformer 104 to the backend part 300, the three-axis accelerating sensor 120 configured to detect the degree of an inclination of the main body 100, that is, the inclination of the main body 100, and the controller 121 configured to output a driving signal to rotate the folder part 200 based on the inclination information of the main body 100 that is detected by the three-axis accelerating sensor 120.

The folder part 200 includes the actuator 204 configured to rotate the folder part 200 according to the driving signal output from the controller 121 of the main body 100, the scan converter 201 configured to change the scan direction of the data, which is received from the beamformer 104, and output the data to the display 202, and the display 202 configured to display an ultrasonic image when the data is output from the scan converter 201.

The backend part 300 includes the second communicator 301 configured to receive the data transmitted from the first communicator 109 of the main body 100, the scan converter 302 configured to change the san direction of the data, which is received from the second communicator 301, and to output the data to the display 303, and the display 303 configured to display an ultrasonic image when the data is output from the scan converter 302.

In an exemplary embodiment, the data output from the beamformer 104 is delivered to the scan converter 201 of the folder part 200 and then is delivered to the backend part 300 though the first communicator 109. An ultrasonic image is displayed on the display 202 of the folder part 200 and the display 300 provided at the backend part 300. In one embodiment, a user may select an ultrasonic image to be displayed at a desired structure, that is, the backend part 300 or the folder part 200.

The method of communication between the first communicator 109 and the second communicator 301 may include a cable method or a wireless method. When the portability of the portable ultrasonic probe is considered, the communication is preferred to be performed by use of the wireless communication method.

The three-axis accelerating sensor 120 mounted at the main body 100 is configured to detect the degree of inclination of the main body 100 when the portable ultrasonic probe is operated. When the degree of inclination of the main body 100 is detected by the three-axis accelerating sensor 120, the controller 121, to rotate the folder part 200 such that the display 202 of the folder part 200 is headed toward a user, drives the actuator 204 provided at a coupler of the folder part 200 based on the information detected. The actuator 204 rotates the folder part 200 according to the control of the controller 121 such that the display 202 may face a user.

When the ultrasonic probe is moved along the surface of a subject, which is in a curved shape, during an ultrasonic examination, the degree of inclination of the main body 100 may be changed according to the degree of curvature of the subject. When the main body 100 is inclined toward a side opposite to a user, the folder part 200 is also inclined accordingly, and thus the user is needed to rotate the folder part 200 toward a direction opposite to the direction of inclination of the folder part 200 such that the user may easily check an ultrasonic image. Performing a manipulation as the above each time when the degree of inclination of the main body 100 is changed may be inconvenient, and thus, in this embodiment, the three-axis accelerating sensor 120 may be used to detect the degree of inclination of the main body 100. Based on the detected degree of inclination of the main body 100, the display 202 of the folder part 200 may be controlled to automatically adjust the direction thereof to face toward a user.

As illustrated in FIG. 17, the coupler 230 of the folder part 200 of an exemplary embodiment may be provided with two rotating axes that are substantially perpendicular to each other, e.g., the first rotating axis parallel to a y-axis and the second rotating axis that is substantially perpendicular to the first rotating axis. As the coupler 230 is provided with the first rotating axis and the second rotating axis, the folder part 200 may be rotated as illustrated in FIG. 17.

In FIG. 7, the ultrasonic echo signals that are output from the transducer module 103 are converted into the digital signals, and a beamforming is performed on the digital signals by the digital beamformer 106, however, exemplary embodiments are not limited hereto. For example, the portable ultrasonic probe may an analog beamformer to perform analog beamforming. That is, the ultrasonic echo signals output from the transducer module 103 are received by the analog beamformer such that the time difference is calibrated, the signals with calibrated time difference are converted into digital signals by the AD converter 105, and the above described beamforming process is performed on the converted digital signals by the digital beamformer 106.

The beamformer 104 having the above described analog beamformer or digital beamformer 106, and the AD converter 105 may be implemented on a single chip and provided at the main body 100 of the portable ultrasonic probe. In addition, the transducer module 103 and the beamformer 104 may be provided in a single module and detachably provided at the main body 100.

Figure 8:
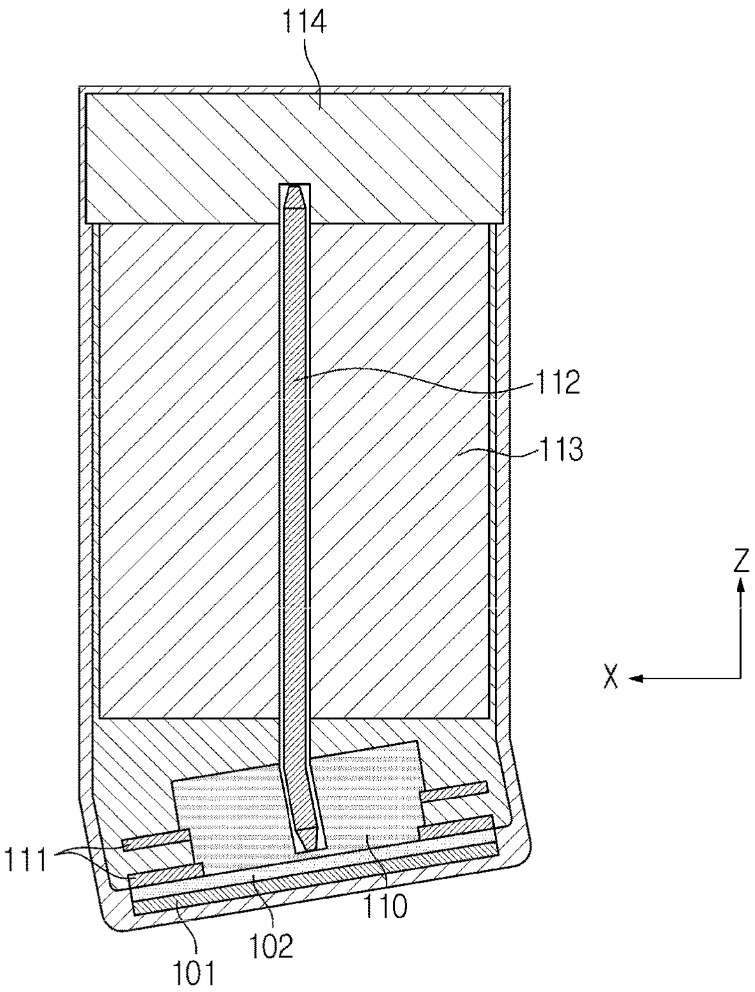
FIG. 8 is a view showing an internal structure of a portable ultrasonic probe to release heat of a main body thereof according to an exemplary embodiment.
Figure 9:
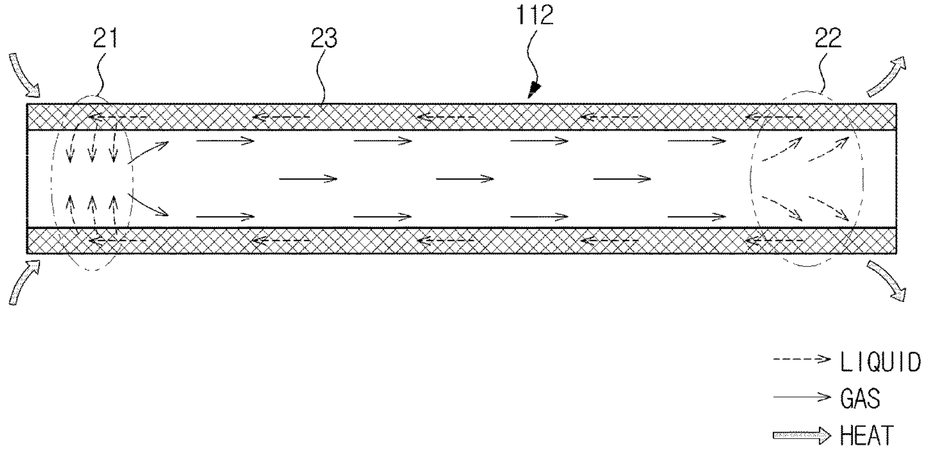
FIG. 9 is a view showing an operation principle of a heat pipe of a portable ultrasonic probe according to an exemplary embodiment.
Figure 10:
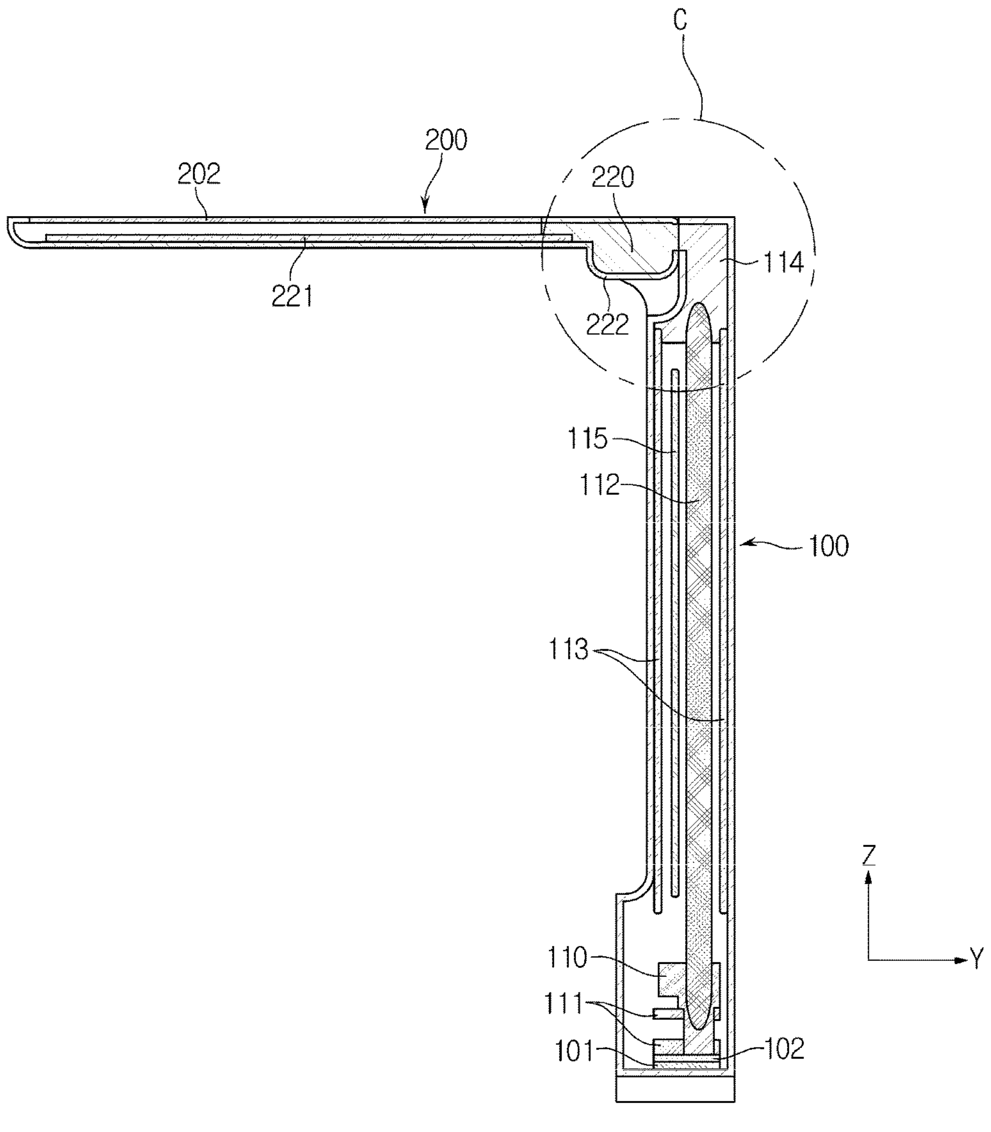
FIG. 10 is a cross sectional view showing a portable ultrasonic probe according to an exemplary embodiment.
Figure 11:
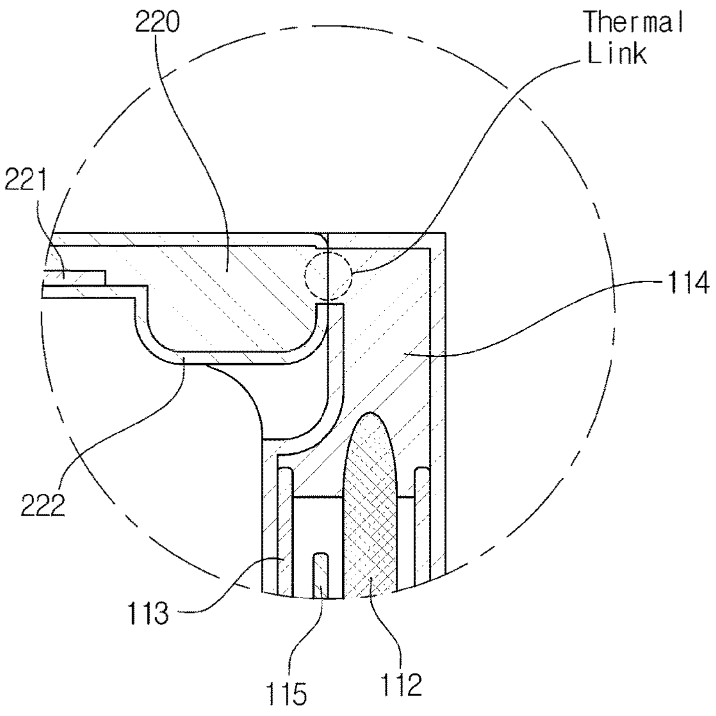
FIG. 11 is an enlarged view of an area "C" in FIG. 10.
Figure 12:
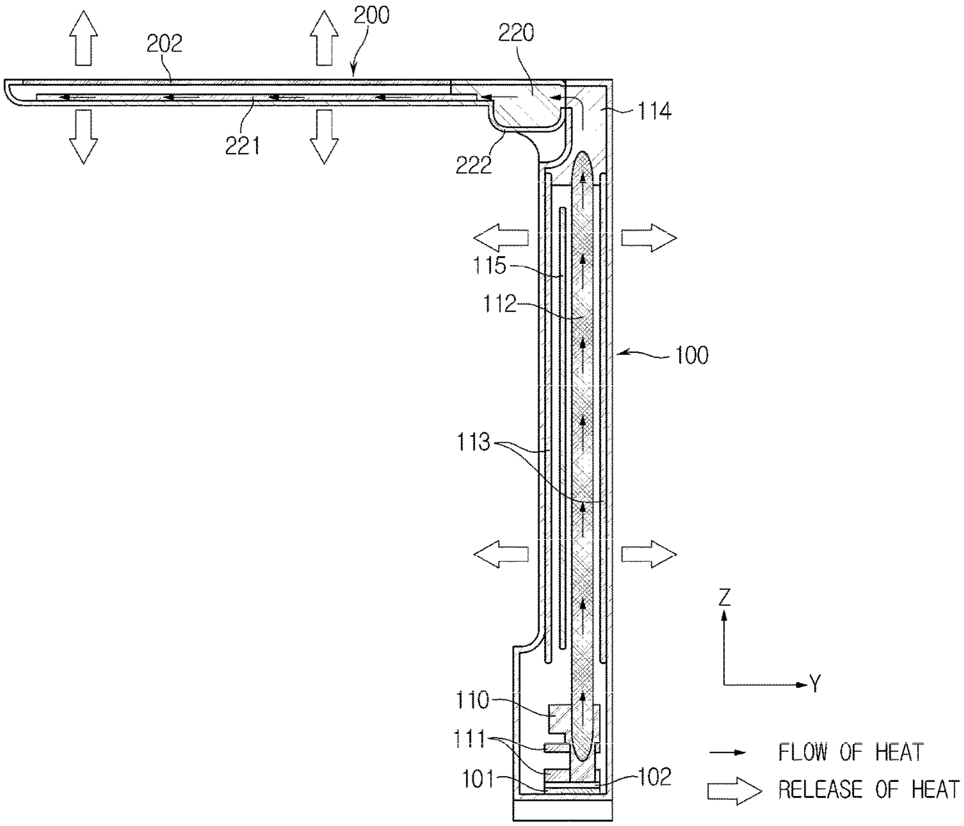
FIG. 12 is a view showing a flow of heat of a portable ultrasonic probe according to an exemplary embodiment.

FIG. 8 is a view showing an internal structure to release heat of a main body of a portable ultrasonic probe according to an exemplary embodiment, FIG. 9 is a view showing an operation principle of a heat pipe of a portable ultrasonic probe according to an exemplary embodiment, FIG. 10 is a cross sectional view showing a portable ultrasonic probe according to an exemplary embodiment, and FIG. 11 is an enlarged view of an area "C" of FIG. 10. FIG. 12 is a view showing a flow of heat of a portable ultrasonic probe according to an exemplary embodiment.

The main body 100 includes the transducer 101 generating an ultrasonic wave and a first heat radiating module that absorbs heat generated from the transducer 101 and releases the heat.

The first heat radiating module configured to release heat after absorbing the heat generated from the transducer 101 includes a heat spreader 110 configured to absorb the heat generated from the transducer 101, a heat pipe 112 installed on the heat spreader 110 and configured to deliver the heat absorbed by the heat spreader 110 toward a direction opposite to a direction in which an ultrasonic wave is radiated, and a first connector 114 installed to have thermal contact with a condenser part 22 of the heat pipe 112 to absorb the heat delivered from the heat pipe 112.

The heat spreader 110 is installed at a surface of the transducer 101 to absorb the heat generated from the transducer 101. The heat spreader 110 may comprise metal, such as aluminum.

The heat spreader 110 is configured to have thermal contact with the transducer 101 to absorb the heat generated from the transducer 101. In an exemplary embodiment, the structure of the heat spreader 110 of FIG. 3 may be adopted when the cMUT is used as the transducer 101. In general, the cMUT array is bonded to an integrated circuit such as the ASIC 102 through a flip-chip bonding method, and the ASIC 102 to which the cMUT array is bonded may be provided with the signal line bonded to the printed circuit board 111 through a wire bonding method. The printed circuit board 111 may be electrically connected to the board 115 through a wire or a flexible printed circuit board. In FIG. 8, the heat spreader 110 installed at the printed circuit board 111 is illustrated. The heat spreader 110 is insertably installed on the printed circuit board 111, and has thermal contact with the transducer 101.

The heat spreader 110 may be provided to have direct contact with the transducer 101, or may be provided to have a predetermined gap with the transducer, without having direct contact with the transducer 101. The gap in between the transducer 101 and the heat spreader 110 may be filled with heat medium such as thermal grease or phase change material having higher conductivity. The heat generated from the transducer 101 may be directly delivered through the heat spreader 110, or may be delivered to the heat spreader 110 through the thermal grease or the phase change material filled in the gap.

At the heat spreader 110, the heat pipe 112, which is configured to deliver the heat absorbed by the heat spreader 110 to a direction opposite to the direction in which an ultrasonic wave is radiated, e.g., a z-axis direction, may be installed. As illustrated in FIG. 8, the heat pipe 112 may be installed while formed in a bent shape according to the degree of inclination of the ultrasonic wave irradiation surface of the ultrasonic wave.

The heat spreader 110 may be provided with an insertion groove into which the heat pipe 112 is inserted and installed on the heat spreader 110. To efficiently deliver heat from the heat spreader 110 to the heat pipe 112, the depth of the insertion groove provided at the heat spreader 110 may substantially reach a surface at which the heat spreader 110 has thermal contact with the transducer 101. That is, the heat pipe 112 may be inserted such that the heat spreader 110 substantially reaches the surface at which the heat spreader 110 has thermal contact with the transducer 101.

FIG. 9 is a view showing an operating principle of the heat pipe 112.

The heat pipe 112 is an apparatus provided with a container in a shape of a sealed pipe into which working fluid is injected and placed into a vacuum state. The working fluid within the heat pipe 112 may have two phases to deliver heat.

Referring to FIG. 9, when heat is applied to an evaporation part 21 of the heat pipe 112, the heat is delivered to an inside of the heat pipe 112 by heat conductivity through an outer wall of the heat pipe 112. Since an inside of the heat pipe 112 has higher pressure, the evaporation of the working fluid may occur on a surface of a wick 23 even at a low temperature. Through the evaporation of the working fluid, the evaporation part 21 is provided with increased density and pressure of gas, and thus, a pressure gradient is provided between the evaporation part 21 and the condenser part 22, at which density and pressure of gas are relatively low, and thus gas is moved toward the condenser part 22. At this time, the moving gas may be provided with a larger amount of heat that corresponds to evaporative latent heat. The gas that is moved to the condenser part 22 is condensed at an inner wall of the condenser part 22, at which a relatively lower temperature is present. Thus, heat is released, and the gas is returned to the state of liquid again. The working fluid that is returned to the state of liquid is moved toward the evaporation part 23 by capillary pressure or gravity of the wick 23 through pores provided at an inside of the wick 23. By repeating the above process, the transfer of heat may be continuously performed.

The evaporation part 23 of the heat pipe 112 may be installed to have contact with the heat spreader 110 which absorbs the heat generated from the transducer 101, and the heat pipe 112 may deliver the heat generated from the transducer 101 in the z-axis direction according to the above described heat transfer process.

The condenser part 22 of the heat pipe 112 is installed to have thermal contact with the first connector 114, which will be described later, and delivers heat to the first connector 114. As illustrated in FIG. 3, the condenser part 22 of the heat pipe 112 may be insertably installed on the first connector 114.

The first connector 114 may comprise metal such as aluminum having improved heat conductivity. Referring to FIG. 10, the first connector 114 is installed on an end portion of the main body 100 positioned at a direction opposite to the direction in which an ultrasonic wave is radiated from the main body 100. The first connector 114 has thermal contact with the condenser part 22 of the heat pipe 112 to absorb the heat delivered from the heat pipe 112. In addition, when the portable ultrasonic probe is opened as the folder part 200 is rotated, the first connector 114 has contact with a second connector 220 of a second heat radiating module that is included in the folder part 200, to deliver heat to the second connector 220.

As illustrated in FIGS. 8 to 10, the first heat radiating module may further include a heat radiating panel 113 provided to release the heat, which is generated from the transducer 101 and/or other structure of the main body 100 including, e.g., the board 115 to output a signal for driving the transducer 101, to the outside through a housing of the main body 100.

As illustrated in FIG. 10, the heat radiating panel 113 may be installed at at least one from among an inner side of a first surface of the main body 100 that has contact with the folder part 200 when the portable ultrasonic probe is folded and an inner side of a second surface of the main body 100 opposite to the first surface. By installing the heat radiating panel 113 on the inner side of the surface that has a larger area, the heat absorbed by the heat radiating panel 113 may be efficiently released.

As illustrated in FIG. 10, the heat radiating panel 113 may be installed on at least a portion of the first connector 114, and may deliver the absorbed heat to the first connector 114.

Although it is shown in the drawing that the heat radiating panel 113 is not in direct contact with the heat spreader 110, exemplary embodiments are not limited hereto, and the heat radiating panel 113 may be installed to have direct contact with the heat spreader 110 to release the heat absorbed from the heat spreader 110.

In addition, by providing the heat radiating panel 113 as a Peltier element or by further installing other heat radiating members provided as the Peltier element, heat radiating efficiency may be enhanced.

Referring to FIG. 12, the heat generated from the transducer 101 is absorbed by the heat spreader 110, and the heat absorbed by the heat spreader 110 is delivered to the first connector 114 through the heat pipe 112 installed on the heat spreader 110. The heat delivered from the heat pipe 112 to the first connector 114 is delivered to the second connector 220, which has contact with the first connector 114 when the potable ultrasonic probe is open. The heat, which is generated from the transducer 101 and/or other structures of the main body 100 including, e.g., the board 115 configured to output a signal to drive the transducer 101, is absorbed by the heat radiating panel 113 and is released to the outside through the housing of the main body 100. The heat delivered to the second connector 220 is released to the outside through the heat radiating panel (not shown) connected to the second connector 220.

The folder part 200 includes the display 202 configured to display an ultrasonic image, and a second heat radiating module configured to absorb and release the heat delivered from the first heat radiating module of the main body 100.

As illustrated in FIG. 1, the display 202 is provided at a first surface opposite to a second surface of the folder part 200 that has contact with the main body 100 when the folder part 200 is folded.

As illustrated in FIG. 1, a user may rotate the folder part 200 to examine a subject in a state where the portable ultrasonic probe is opened, and may check the ultrasonic image that is displayed on the display 202.

As shown in FIG. 2, since the surface of the main body 100 from which an ultrasonic wave is radiated is inclined, when the portable ultrasonic probe is opened as shown in FIG. 1, the display 202 may face a direction of a user, and thus the user may not need to change the posture or tilt the portable ultrasonic probe to check the display 202.

The second heat radiating module includes the second connector 220 that absorbs the heat delivered from the first heat radiating module. In FIG. 11, a "C" area of FIG. 10, that is, the area at which the first connector 114 and the second connector 220 have contact with each other is illustrated in an enlarged manner. Referring to FIG. 11, the first connector 114 and the second connector 220 have contact with each other when the portable ultrasonic probe is opened. In a state where the folder part 200 is folded, the first connector 114 and the second connector 220 may not have contact to each other. On the other hand, when the folder part 200 is moved to open the portable ultrasonic probe, the first connector 114 and the second connector 220 may have contact with each other.

Similar to the first connector 114, the second connector 220 may comprise metal having improved heat conductivity, and when the second connector 220 has contact with the first connector 114, the heat delivered from the heat pipe 112 to the first connector 114 may be absorbed by the second connector 220.

When the portable ultrasonic probe is opened, the first connector 114 and the second connector 220 may be provided such that a predetermined gap may exists between the first connector 114 and the second connector 220, i.e., the first connector 114 and the second connector 220 do not have direct contact with each other. The gap may be filled with heat medium such as thermal grease or phase change material having higher conductivity. In this case, the heat of the first connector 114 may be delivered to the second connector 220 through the heat medium, as already described in the above.

The second heat radiating module includes a heat radiating panel 221 configured to absorb and release the heat delivered to the second connector 220. As illustrated in FIG. 4, the heat radiating panel 221 may be installed at an inner side of the surface at which the folder part has contact with the main body 100 when the portable ultrasonic probe is folded. By installing the heat radiating panel 221 at an inner side of the surface having a larger area, the heat absorbed by the heat radiating panel 221 may be further efficiently released. Although not illustrated in the drawing, the second heat radiating module also may be provided with a heat pipe.

By installing the heat pipe at the second connector 220, heat from the second connector 220 may be absorbed, and the absorbed heat may be delivered to a first side of the folder part 200 opposite to a second side at which the second connector 220 is installed. In addition, by installing a heat radiating member on the condenser part of the heat pipe, the heat delivered from the heat pipe may be efficiently released.

The folder part 200 includes a coupler 222 configured to couple the folder part 200 to the main body 100 such that the folder part 200 may be rotatably coupled to the main body 100.

The coupler 222 is configured to hinge-couple the folder part 200 to the main body 100, and as illustrated in FIG. 1, the coupler 222 is provided with a rotating axis substantially parallel to an x-axis such that the folder part 200 may be rotatably moved. In FIG. 1, the coupler 222 is provided with one rotating axis that is parallel to the x-axis, but exemplary embodiments are not limited thereto. For example, as shown in FIG. 17, the coupler 230 may be provided with two rotating axes that are substantially perpendicular to each other, e.g., a first rotating axis substantially parallel to a y-axis and a second rotating axis substantially perpendicular to the first rotating axis.

When the coupler 230 is provided with the first rotating axis and the second rotating axis, the folder part 200 may be rotated as illustrated in FIG. 17. A user may easily check the image displayed on the display 202 by rotating the folder part 200 to a desired position.

Figure 13:
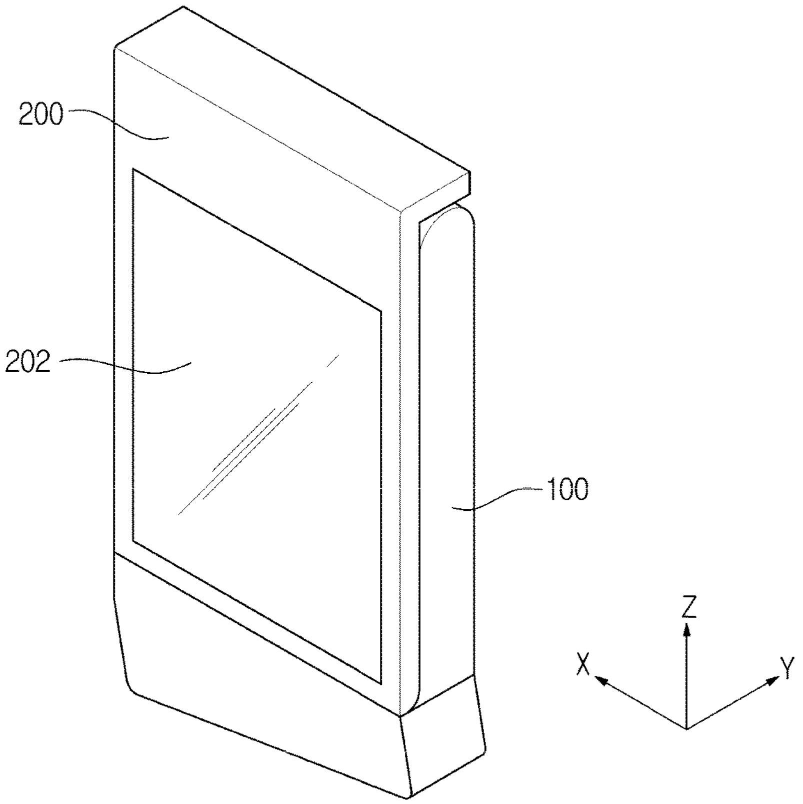
FIGS. 13 and 14 are perspective views showing an exterior appearance of a portable ultrasonic probe according to another exemplary embodiment.
Figure 14:
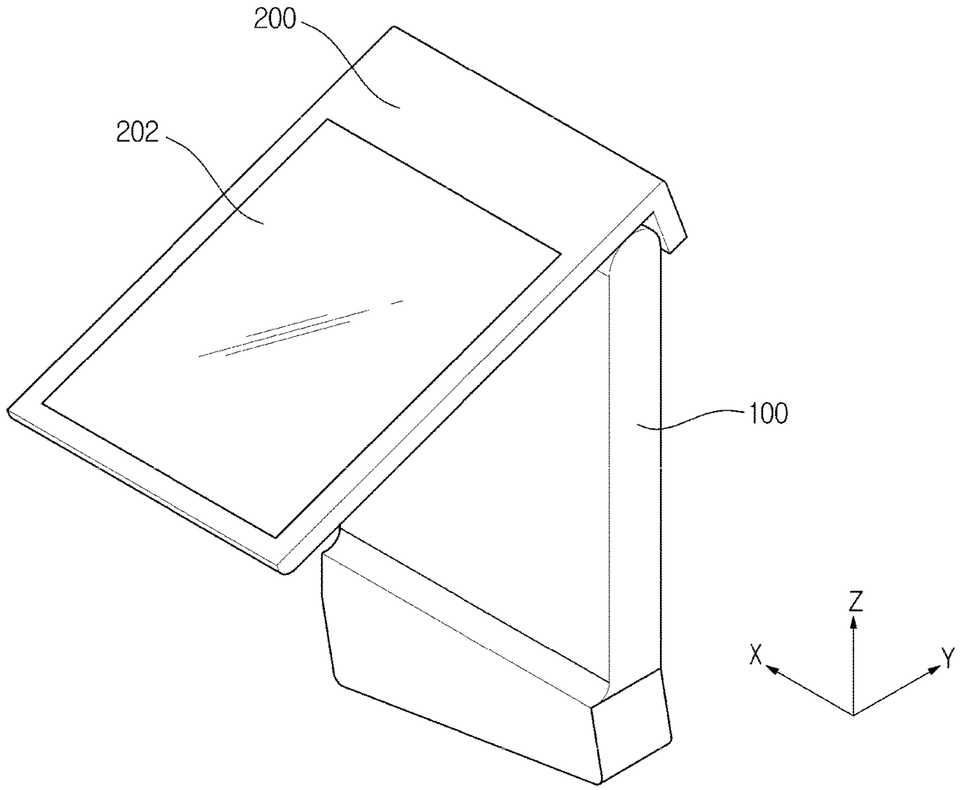
Figure 15:
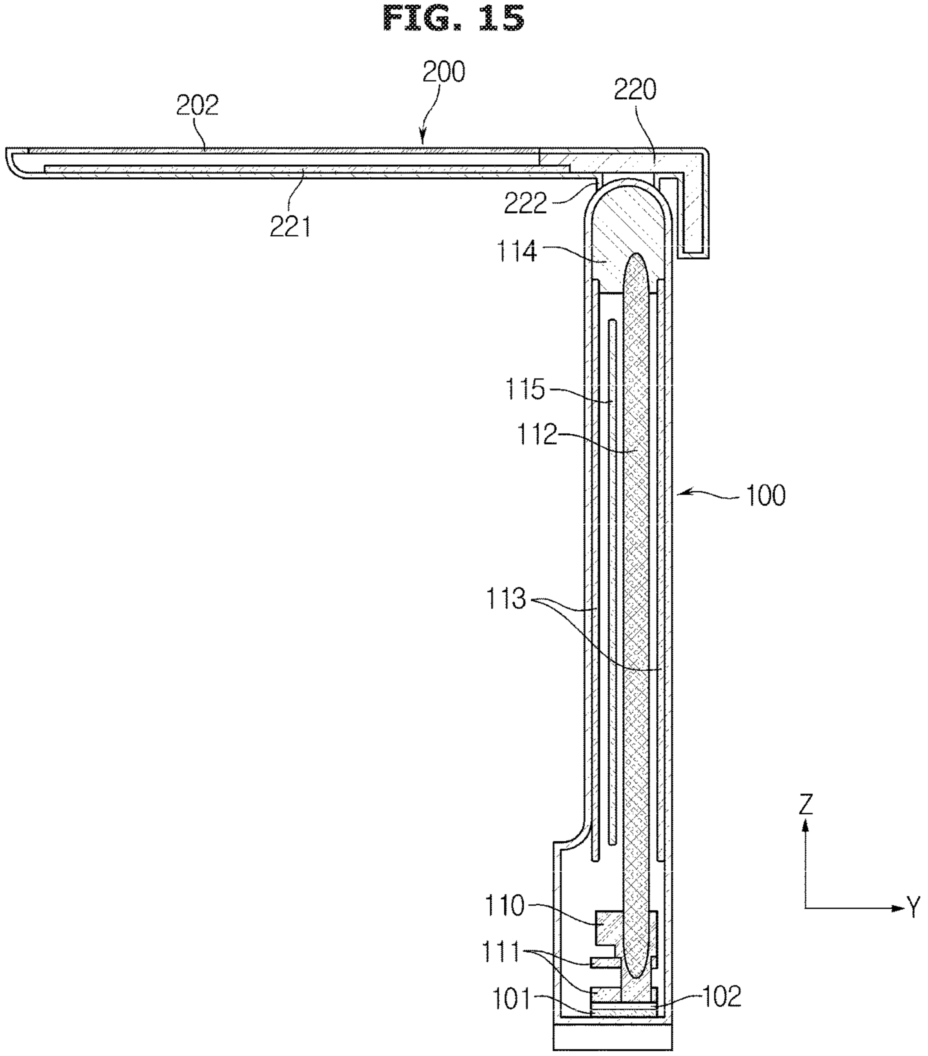
FIG. 15 is a cross sectional view showing a portable ultrasonic probe according to another exemplary embodiment.
Figure 16:
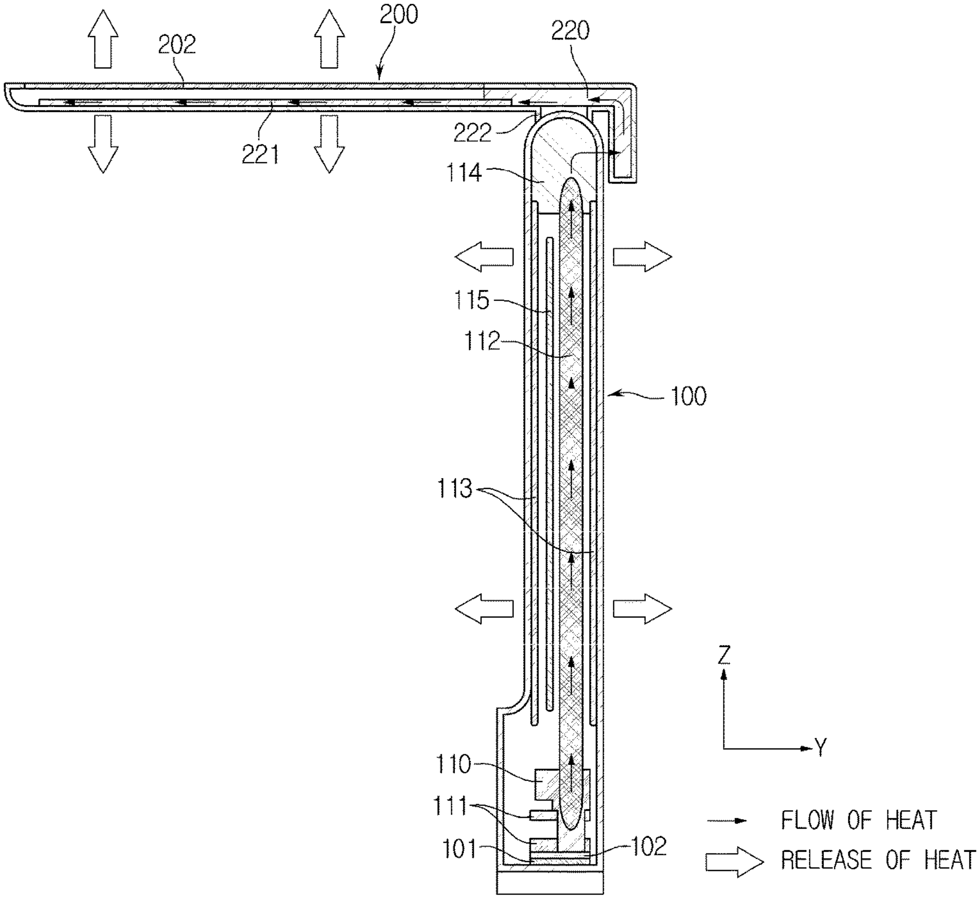
FIG. 16 is a view showing a flow of heat of a portable ultrasonic probe according to another exemplary embodiment.

FIGS. 13 and 14 are perspective views showing an exterior appearance of a portable ultrasonic probe in accordance with another exemplary embodiment of the present disclosure, FIG. 15 is a cross sectional view showing the portable ultrasonic probe in accordance with another embodiment of the present disclosure, and FIG. 16 is a view showing a flow of heat of the portable ultrasonic probe in accordance with another embodiment of the present disclosure, and FIG. 17 is a perspective view showing an exterior appearance of the portable ultrasonic probe in accordance with still another exemplary embodiment.

Referring to FIGS. 13 and 14, a portable ultrasonic probe according to another exemplary embodiment includes the main body 100 having the transducer 101 configured to generate an ultrasonic wave, and the folder part 200 rotatably coupled to the main body 100 and having the display 202 configured to display an ultrasonic image.

The main body 100 includes the transducer 101 to generate an ultrasonic wave, and a first heat radiating module to absorb and release the heat generated from the transducer 101.

The ultrasonic probe illustrated in FIGS. 13 to 16, similar to the exemplary embodiment of FIG. 2, a surface from which an ultrasonic wave of the transducer 101 included at the main body 100 is radiated forms a predetermined angle ‘a’ with respect to an x-axis. That is, the surface from which the ultrasonic wave is radiated and a top surface of the portable ultrasonic probe are not parallel to each other, but the surface from which the ultrasonic wave is radiated is inclined with respect to the top surface of the portable ultrasonic probe.

Since the surface from which the ultrasonic wave is radiated is inclined as the above, a user may easily check the display 202 of the folder part 200 when the folder part 200 is opened. That is, when an inclined surface from which the ultrasonic wave is radiated has contact with the examination portion of a subject, the display 202 of the folder part 200 is inclined toward a user according to a degree by which the surface from which the ultrasonic wave is radiated is inclined. Thus, the user may easily check the image displayed on the display 202 without having to change the posture to check the display 202 or tilt the ultrasonic probe while proceeding with the examination.

The first heat radiating module of the main body 100 configured to absorb and release heat generated from the transducer 101 includes the heat spreader 110 configured to absorb the heat generated from the transducer 101, the heat pipe 112 installed on the heat spreader 110 and configured to deliver the heat absorbed by the heat spreader 110 toward a direction opposite to a direction in which an ultrasonic wave is radiated, and the first connector 114 installed to have thermal contact with the condenser part 22 of the heat pipe 112 to absorb the heat delivered from the heat pipe 112.

The heat spreader 110 may be installed at a surface of the transducer 101 to absorb the heat generated from the transducer 101. The heat spreader 110 may comprise metal, such as aluminum.

The heat spreader 110 is configured to have thermal contact with the transducer 101 to absorb the heat generates from the transducer 101. In an exemplary embodiment, the structure of the heat spreader 110 of FIG. 3 may be adopted when a cMUT is used as the transducer 101. In general, the cMUT array is bonded to an integrated circuit such as the ASIC 102 through a flip-chip bonding method, and the ASIC 102 to which the cMUT array is bonded may be provided with the signal line bonded to the printed circuit board 111 through a wire bonding method. In FIGS. 15 and 16, the heat spreader 110 installed on the printed circuit board 111 is illustrated. The heat spreader 110 is insertably installed on the printed circuit board 111, and has thermal contact with the transducer 101.

The heat spreader 110 may be provided to have direct contact with the transducer 101, or may be provided to have a predetermined gap without having direct contact with the transducer 101. The gap between the transducer 101 and the heat spreader 110 may be filled with heat medium such as thermal grease or phase change material having higher conductivity. The heat generated at the transducer 101 may be directly delivered through the heat spreader 110, or may be delivered to the heat spreader 110 through the thermal grease or the phase change material filled in the gap.

At the heat spreader 110, the heat pipe 112, which is configured to deliver the heat absorbed at the heat spreader 110 to a direction opposite to the direction in which an ultrasonic wave is radiated, that is, a z-axis direction, may be installed. As illustrated in FIGS. 15 and 16, the heat pipe 112 may be installed in a bent shape according to the degree of inclination of the ultrasonic wave irradiation surface.

The heat spreader 110 may be provided with an insertion hole into which the heat pipe 112 may be inserted and installed on the heat spreader 110. To efficiently deliver heat from the heat spreader 110 to the heat pipe 112, the depth of the insertion hole provided at the heat spreader 110 may be sufficient to substantially reach the surface at which the heat spreader 110 has thermal contact with the transducer 101. That is, the heat pipe 112 may be inserted such that the heat spreader 110 substantially reaches the surface at which the heat spreader 110 has thermal contact with the transducer 101.

The evaporation part 21 of the heat pipe 112 is installed to have contact with the heat spreader 110 which absorbs the heat generated from the transducer 101, and the heat pipe 112 delivers the heat generated from the transducer 101 toward the z-axis.

The condenser part 22 of the heat pipe 112 is installed to have thermal contact with the first connector 114 and delivers heat to the first connector 114. As illustrated in FIGS. 15 and 16, the condenser part 22 of the heat pipe 112 may be insertably installed on the first connector 114.

The first connector 114 may comprise metal such as aluminum having improved heat conductivity. Referring to FIGS. 15 and 16, the first connector 114 is installed at an end portion of the main body 100 positioned in a direction opposite to the direction in which an ultrasonic wave is radiated from the main body 100. The first connector 114 has thermal contact with the condenser part 22 of the heat pipe 112 to absorb the heat delivered from the heat pipe 112. In addition, when the portable ultrasonic probe is opened as the folder part 200 is rotated, the first connector 114 has contact with the second connector 220 of the second heat radiating module that is included in the folder part 200, to deliver heat to the second connector 220.

As illustrated in FIGS. 15 and 16, the first heat radiating module may further include the heat radiating panel 113 provided to release the heat, which is generated from the transducer 101 and/or other structure of the main body 100 including, e.g., the board 115 to output a signal to drive the transducer 101, to an outside through the housing of the main body 100.

As illustrated in FIGS. 15 and 16, the heat radiating panel 113 may be installed at at least one from among an inner side of a first surface of the main body 100 that has contact with the folder part 200 when the portable ultrasonic probe is folded and an inner side of a second surface of the main body 100 opposite to the first surface. By installing the heat radiating panel 113 at at least one from among the inner side of the first surface and the inner side of the second surface having a larger area, the heat absorbed by the heat radiating panel 113 may be efficiently released.

As illustrated in FIGS. 15 and 16, the heat radiating panel 113 may be installed on at least a portion of the first connector 114, and may deliver the absorbed heat to the first connector 114.

Although it is shown in the drawing that the heat radiating panel 113 is not in direct contact with the heat spreader 110, but exemplary embodiments are not limited hereto. For example, and the heat radiating panel 113 may be installed to directly have contact with the heat spreader 110 to release the heat absorbed from the heat spreader 110.

In addition, by providing the heat radiating panel 113 as a Peltier element or by installing other heat radiating members provided as the Peltier element, the heat radiating efficiency may be enhanced.

Referring to FIG. 16, the heat generated from the transducer 101 is absorbed by the heat spreader 110, and the heat absorbed by the heat spreader 110 is delivered to the first connector 114 through the heat pipe 112 installed on the heat spreader 110. The heat delivered from the heat pipe 112 to the first connector 114 is delivered to the second connector 220, as the first connector 114 has contact with the second connector 220 when the potable ultrasonic probe is opened. The heat, which is generated from the transducer 101 and/or other structures of the main body 100 including, e.g., the board 115 configured to output a signal to drive the transducer 101, is absorbed to the heat radiating panel 113, and is released to the outside through the housing of the main body 100. The heat delivered to the second connector 220 is released to the outside through the heat radiating panel 221 connected to the second connector 220.

The folder part 200 includes the display 202 configured to display an ultrasonic image, and the second heat radiating module configured to absorb and release the heat delivered from the first heat radiating module of the main body 100.

As illustrated in FIGS. 13 and 14, the display 202 is provided at a first surface opposite to a second surface of the folder part 200 that has contact with the main body 100 when the folder part 200 is folded.

As illustrated in FIGS. 13 and 14, a user may rotate the folder part 200 to perform an examination in a state where the portable ultrasonic probe is opened, and may check the ultrasonic image that is displayed on the display 202.

As shown in FIGS. 13 and 14, since the surface of the main body 100 from which an ultrasonic wave is radiated is inclined, when the portable ultrasonic probe is opened as shown in FIG. 14, the display 202 may face a direction of a user, and thus the user may not needed to change the posture or tilt the portable ultrasonic probe to check the display 202.

The second heat radiating module includes the second connector 220 that absorbs the heat delivered from the first heat radiating module. Referring to FIGS. 15 and 16, in an exemplary embodiment, differently from the second connector 220 illustrated in FIGS. 10 to 12, the second connector 220 is provided to surround at least a portion of the first connector 114. Thus, when the portable ultrasonic probe is opened, the second connector 220 is moved to a position at which the second connector 220 may have thermal contact with the first connector 114 to receive heat from the first connector 114.

The second heat radiating module includes the heat radiating panel 221 configured to absorb and release the heat delivered to the second connector 220. As illustrated in FIG. 15, the heat radiating panel 221 may be installed at an inner side of a first surface at which the folder part have contact with the main body 100 when the portable ultrasonic probe is folded. Also, although not shown in the drawings, the heat radiating panel may be installed at an inner side of a second surface opposite to the first surface of the folder part 200. By installing the heat radiating panel 221 at an inner side of the surface having a larger area, the heat absorbed by the heat radiating panel 221 may be further efficiently released. Although not illustrated in the drawing, the second heat radiating module also may be provided with a heat pipe. By installing the heat pipe on the second connector 220 to absorb heat from the second connector 220, the absorbed heat may be delivered to a first side opposite to a second side at which the second connector 220 is installed. In addition, by installing a heat radiating member on the condenser part 22 of the heat pipe, the heat delivered from the heat pipe may be further released.

The folder part 200 includes the coupler 222 configured to couple the folder part 200 to the main body 100 such that the folder part 200 may be rotatably coupled to the main body 100.

The coupler 222 is configured to hinge-couple the folder part 200 to the main body 100. In an exemplary embodiment, as illustrated in FIG. 1, the coupler 222 may be provided with a rotating axis provided to be in parallel to an x-axis and the folder part 200 may be rotatably moved around the rotating axis. In FIG. 1, the coupler 222 is provided with one rotating axis that is parallel to the x-axis, but exemplary embodiments are not limited thereto. For example, as shown in FIG. 17, the coupler 230 may be provided with two rotating axes that are substantially perpendicular to each other, e.g., the first rotating axis parallel to a y-axis and the second rotating axis substantially perpendicular to the first rotating axis.

When the coupler 230 is provided with the first rotating axis and the second rotating axis, the folder part 200 may be rotated around at least one of the first and the second rotating axes as illustrated in FIG. 17. A user may easily check the image displayed on the display 202 by rotating the folder part 200 to a desired position.

A portable ultrasonic probe according to exemplary embodiments may have a reduced size such that portability of the portable ultrasonic probe may be enhanced.

Also, a portable ultrasonic probe according to exemplary embodiments may have enhanced stability by efficiently releasing heat generated from the portable ultrasonic probe to the outside.

Although a few exemplary embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A portable ultrasonic probe, comprising:

a main body comprising a transducer configured to generate an ultrasonic wave, a heat pipe configured to deliver heat generated from the transducer toward a first direction, and a first connector configured to absorb the heat delivered from the heat pipe, the first direction being opposite to a second direction in which the ultrasonic wave is radiated; and a folder part comprising a first display and rotatably coupled to an end portion of the main body, wherein the main body further comprises an analog to digital (AD) converter and a beamformer, the AD converter and the beamformer being provided in a chip, wherein the transducer, the AD converter, and the beamformer are provided in a module, and the module is detachably provided in the main body, and wherein the folder part comprises a second connector that comes into contact with the first connector when the folder part is opened, the second connector configured to deliver heat from the first connector to a first side of the folder part opposite to a second side of the folder part at which the second connector is positioned.

2. The portable ultrasonic probe of claim 1, wherein:

the beamformer of the main body comprises an analog beamformer and a digital beamformer, and the analog beamformer, the AD converter, and the digital beamformer are provided in the chip.

3. The portable ultrasonic probe of claim 1, wherein:

the main body further comprises a battery configured to supply power to drive the portable ultrasonic probe.

4. The portable ultrasonic probe of claim 3, wherein:

the battery is detachably provided in the main body.

5. The portable ultrasonic probe of claim 1, wherein:

the folder part further comprises a scan converter configured to output data received from the beamformer, to the first display, and the first display displays an ultrasonic image based on the data output from the scan converter.

6. The portable ultrasonic probe of claim 1, wherein:

the first display comprises a touch panel configured to provide a user interface for controlling the portable ultrasonic probe.

7. The portable ultrasonic probe of claim 1, wherein:

the main body further comprises a communicator circuitry configured to transmit data output from the beamformer to a backend part, the backend part comprising a second display configured to display an ultrasonic image.

8. The portable ultrasonic probe of claim 1, wherein the folder part further comprises:

a coupling mechanism to rotatably couple the folder part to the main body; and an actuator configured to provide a driving force to rotate the folder part in a third direction according to at least one rotating axis thereof.

9. The portable ultrasonic probe of claim 8, wherein the coupling mechanism comprises at least two rotating axes that are perpendicular to each other, and the actuator provides the driving force to rotate the folder part in a fourth direction according to at least one from among the at least two rotating axes.

10. The portable ultrasonic probe of claim 8, wherein the main body further comprises:

a three-axis accelerating sensor configured to detect inclination of the main body, and a processor configured to output a control signal to drive the actuator based on the detected inclination of the main body.

11. The portable ultrasonic probe of claim 1, wherein:

a surface of the main body from which the ultrasonic wave is radiated has a predetermined angle with respect to an opposite surface of the main body.

12. The portable ultrasonic probe of claim 1, wherein the main body further comprises a heat spreader configured to absorb the heat generated from the transducer, and the heat pipe is configured to contact the heat spreader and convey the heat absorbed by the heat spreader toward the first direction.

13. The portable ultrasonic probe of claim 1, wherein the heat pipe is formed in a bent shape based on a degree of inclination of the main body.

14. An ultrasonic system, comprising:

a portable ultrasonic probe comprising a first communicator circuitry configured to transmit data output from a beamformer; and a backend part comprising a second communicator circuitry to receive the data transmitted from the first communicator circuitry, and a first display to display an ultrasonic image based on the data received by the second communicator circuitry, wherein the portable ultrasonic probe further comprises:

a main body, the main body comprising the beamformer, an analog to digital (AD) converter, and a transducer configured to generate an ultrasonic wave, a heat pipe configured to deliver heat generated from the transducer toward a first direction, and a first connector configured to absorb the heat delivered from the heat pipe, the first direction being opposite to a second direction in which the ultrasonic wave is radiated; and a folder part comprising a second display and rotatably coupled to an end portion of the main body, and wherein the transducer, the AD converter, and the beamformer are provided in a module, and the module is detachably provided in the main body, and wherein the folder part comprises a second connector that comes into contact with the first connector when the folder part is opened, the second connector configured to deliver heat from the first connector to a first side of the folder part opposite to a second side of the folder part at which the second connector is positioned.

15. A portable ultrasonic probe, comprising:

a main body comprising a transducer configured to generate an ultrasonic wave, a heat pipe configured to deliver heat generated from the transducer toward a first direction, and a first connector configured to absorb the heat delivered from the heat pipe, the first direction being opposite to a second direction in which the ultrasonic wave is radiated; and a folder part rotatably coupled to the main body, wherein the main body further comprises an analog to digital (AD) converter and a digital beamformer, wherein the transducer, the AD converter, and the digital beamformer are provided in a module, and the module is detachably provided in the main body, and wherein the folder part comprises a second connector that comes into contact with the first connector when the folder part is opened, the second connector configured to deliver heat from the first connector to a first side of the folder part opposite to a second side of the folder part at which the second connector is positioned.

16. The portable ultrasonic probe of claim 15, wherein the analog to digital (AD) converter converts an ultrasonic echo signal received from the transducer into a digital signal.

17. The portable ultrasonic probe of claim 16, wherein the digital beamformer performs beamforming on the converted digital signal.

18. The portable ultrasonic probe of claim 16, wherein the main body further comprises an analog beamformer configured to perform analog beamforming on the ultrasonic echo signal received from the transducer and provide the analog beamformed ultrasonic echo signal to the AD converter.

19. The portable ultrasonic probe of claim 15, wherein the folder part comprises an actuator configured to drive the folder part to rotate according to a direction of at least one axis thereof.

20. The portable ultrasonic probe of claim 15, further comprising:

a coupling mechanism configured to rotatably couple the folder part to the main body, the coupling mechanism comprising an actuator configured to drive the folder part to rotate according to a direction of at least one axis thereof.

* * * * *